United States Patent [19]
Garson et al.

[11] Patent Number: 5,961,996
[45] Date of Patent: Oct. 5, 1999

[54] NAIL TREATMENT COMPOSITION COMPRISING HYDROXY CARBOXYLIC ACID

[75] Inventors: Jean-Claude Garson, Suresnes; Roland Ramin, Itteville, both of France

[73] Assignee: L'Oreal, Paris, France

[21] Appl. No.: 09/038,853

[22] Filed: Mar. 12, 1998

Related U.S. Application Data

[63] Continuation of application No. 08/687,779, Jul. 31, 1996, Pat. No. 5,753,211.

[30] Foreign Application Priority Data

Jul. 31, 1995 [FR] France ................... 95 09306

[51] Int. Cl.$^6$ .............................. A61K 6/00; A61K 7/00; A61K 7/04
[52] U.S. Cl. ............................................ 424/401; 424/61
[58] Field of Search ....................... 424/401, 61; 514/557

[56] References Cited

U.S. PATENT DOCUMENTS

| | | | |
|---|---|---|---|
| 4,302,442 | 11/1981 | Socci et al. ................................ | 424/61 |
| 4,919,920 | 4/1990 | Devos ........................................ | 424/61 |
| 5,091,171 | 2/1992 | Yu et al. .................................... | 424/642 |
| 5,093,108 | 3/1992 | Pappas et al. ............................. | 424/61 |
| 5,108,751 | 4/1992 | Hagan et al. .............................. | 424/401 |
| 5,330,750 | 7/1994 | Sheard et al. ............................. | 424/61 |
| 5,419,895 | 5/1995 | Kubo et al. ............................... | 424/70.51 |
| 5,425,938 | 6/1995 | Znaiden et al. ........................... | 424/78.02 |
| 5,480,633 | 1/1996 | Simion et al. ............................. | 424/70.1 |

FOREIGN PATENT DOCUMENTS

| | | |
|---|---|---|
| 056 595 | 7/1982 | European Pat. Off. . |
| 508 324 | 10/1992 | European Pat. Off. . |
| 662 315 | 7/1995 | European Pat. Off. . |
| WO 95/03811 | 2/1995 | WIPO . |

OTHER PUBLICATIONS

Riechstoffe, Aromen, *Korperpflegemittel*, "Fingernagelhaut–Abloser oder Anweicher", vol. 22, No. 11, Nov. 1972, p. 401.

Patent Abstracts of Japan, vol. 7, No. 77, Mar. 30, 1983.

*Primary Examiner*—Thurman K. Page
*Assistant Examiner*—Sharon Howard
*Attorney, Agent, or Firm*—Finnegan, Henderson, Farabow, Garrett & Dunner, L.L.P.

[57] ABSTRACT

A nail treatment composition comprising hydroxy carboxylic acid.

18 Claims, No Drawings

NAIL TREATMENT COMPOSITION COMPRISING HYDROXY CARBOXYLIC ACID

This is a continuation of application Ser. No. 08/687,779, filed Jul. 31, 1996, now U.S. Pat. No. 5,753,211, which is incorporated herein by reference.

The present invention relates to nail treatment compositions comprising hydroxy carboxylic acids.

It is well known that the nails often have faults in structure and in consistency, which may be of various origins and are linked in particular with the internal functioning of the individual, living conditions, diet, age and state of fatigue of overwork.

These faults may also appear under the effect of erosive events, for example following prolonged or repeated exposure to detergents, solvents, chemicals, especially household chemicals, hot or cold, wet or dry environments or following exposure to UV radiation.

These faults in structure and consistency have the effect of making the surface of the nails unattractive, which may be a source of embarrassment and of much displeasure. Thus, the nails have a tendency to harden, to become dry and easily broken and to split; they therefore become brittle.

Among nail treatments, it is known, according to EP-A-508 324 to apply to the nail a composition comprising a 2-hydroxycarboxylic acid in a concentration ranging from 8% to 20% by weight. This treatment increases the elasticity and flexibility of the nail. However, the use of 2-hydroxycarboxylic acid at such a concentration does not make it possible to obtain a nail varnish having good cosmetic properties: the varnish film takes a long time to dry and remains tacky, and the dry film is translucent, whitish and of low gloss; it becomes flaky and therefore exhibits a poor hold.

The aim of the present invention is to provide a composition which when applied to the nails may enable their general condition to be enhanced, in particular by reducing their hardness, while having good cosmetic properties.

The present invention therefore relates to a nail treatment composition comprising at least one hydroxy carboxylic acid and/or one of its salts, the concentration of the acid being sufficient to achieve softening or a reduction in hardness of the nail, while obtaining good cosmetic properties.

In particular, the present invention relates to a nail treatment composition comprising at least one hydroxy carboxylic acid and/or one of its salts, the concentration of the acid ranging from 0.5% to 3% by weight relative to the total weight of the composition.

Thus it has been noted that the use of hydroxy carboxylic acid at a concentration ranging from 0.5% to 3% makes is possible to obtain a better general condition of the nails, owing in particular to the fact that they become less brittle, since they are less dry and/or prone to breakage, while preserving the cosmetic properties of the composition.

The nail treatment composition used in accordance with the invention spreads readily over the nail and dries rapidly. Following application of the composition to the nail, the film obtained is of high gloss and exhibits a good hold.

The hydroxy carboxylic acids used in accordance with the invention are preferably α-hydroxy carboxylic acid. They are preferably chosen from carboxylic acids having from 2 to 8 carbon atoms, especially those having from 2 to 5 carbon atoms.

The hydroxy carboxylic acids according to the invention may be linear or branched. In particular, it is possible to mention glycolic, lactic, malic, tartaric, citric and/or mandelic acids. Preferably it is possible to use, individually or mixed, glycolic, lactic, citric and mandelic acids.

The carboxylic acids which are used in accordance with the invention can be products of synthesis or of natural origin.

The hydroxy carboxylic acids which are used in accordance with the invention can be present in the final composition in the form of free acid and/or in the form of one of its associated salts (in particular, salts with an organic base or an alkali metal).

According to the invention, the content of hydroxy carboxylic acids in the composition may more preferably range from 0.8% to 2.5% by weight relative to the total weight of the composition.

Moreover, the nail treatment composition of the invention can comprise a vehicle which is cosmetically acceptable for nail treatment compositions.

This vehicle can comprise organic solvents, water and/or an oily medium, for example.

Organic solvents which may be mentioned are ketones such as acetone, methyl ethyl ketone and methyl isobutyl ketone; glycol ethers; alcohols such as ethanol, n-butanol, n-propanol and isopropanol; acetates such as butyl, ethyl or isopropyl acetate and 2-methoxyethyl acetate; linear or branched hydrocarbons such as hexane or octane; and also aromatic hydrocarbons such as xylene and toluene.

When the vehicle comprises water, the nail treatment composition can be present in particular in the form of an aqueous or aqueous-alcoholic solution, an oil-in-water or water-in-oil emulsion, or even of a multiple emulsion, or in the form of an aqueous gel.

The oily medium may comprise one or more volatile and/or nonvolatile oils, for example oils of vegetable, mineral, animal and/or synthetic origin, among which there may be mentioned:

animal or vegetable oils formed by esters of fatty acid and of polyols, especially liquid triglycerides, for example sunflower, corn, soya, squash, grapeseed, sesame, hazelnut, apricot, almond or avocado oil, fish oils, glycerol tricaprocaprylate, or vegetable or animal oils of formula $R_1COOR_2$ in which $R_1$ represents the radical of a higher fatty acid containing from 7 to 19 carbon atoms and $R_2$ represents a branched hydrocarbon chain containing from 3 to 20 carbon atoms, for example Purcellin oil;

natural or synthetic essential oils such as, for example, eucalyptus, hybrid lavender, lavender, vetiver, lemon, sandalwood, rosemary, camomile, savory, nutmeg, cinnamon, hyssop, caraway, orange, geraniol, cade and bergamot oils;

hydrocarbons such as hexadecane and liquid paraffin;

esters of mineral acid and an alcohol;

ethers and polyethers;

silicone oils and gums.

Moreover, in accordance with the intended application, the nail treatment composition may include a film-forming polymer.

In the nail treatment composition according to the invention, the film-forming polymer can make it possible to deposit on the nail a resistant film which provides for long-term contact of the carboxylic acid with the nail surface.

By way of example, the polymer may be chosen from nitrocellulose, cellulose acetobutyrate, polyvinylbutyral polymers, alkyd resins, polyesters, acrylics and polyurethanes.

The polymers can be dissolved or dispersed in the composition. They can generally be present in a concentration ranging from 1% to 40% by weight relative to the total weight of the composition.

The nail treatment composition according to the invention may also comprise, in addition to the film-forming polymer, plasticizers which make it possible to regulate the flexibility of the film without weakening its physical strength.

The plasticizers which can be used are those which are commonly employed in nail varnish compositions. Plasticizers which may be mentioned are dibutyl phthalate, dioctyl phthalate, diisobutyl phthalate, dimethoxyethyl phthalate, benzyl benzoate and glyceryl benzoate; triethyl citrate, tributyl citrate, tributyl acetyl citrate; tributyl phosphate, triphenyl phosphate and glycols; camphor, and derivatives and mixtures thereof.

The plasticizers can generally be present in a concentration ranging from 1% to 40% by weight relative to the total weight of the composition.

Moreover, the composition according to the invention can contain adjuvants which are commonly used in nail treatment compositions for cosmetic purposes. Mention may be made, by way of example, of adjuvants, dyes, pigments, pearlescence agents, lacquers, anti-UV agents, thickeners, surfactants, waxes, fragrances and active agents such as D-panthenol, phytantriol, vitamins and their derivatives, keratin and its derivatives, melanin, collagen, cystine, chitosan and its derivatives, ceramides, biotin, trace elements, glycerol, protein hydrolysates, phospholipids and moisturizers.

A person skilled in the art will know how to choose this or these possible adjuvants and/or the quantity thereof in such a way that the advantageous properties of the composition according to the invention are not, or substantially are not, impaired by the envisaged addition.

The nail treatment composition according to the invention may be in the form of a nail varnish.

Examples illustrating the present invention will now be given without, however, limiting it.

EXAMPLE 1

The hardness of a nail treated with citric acid was determined.

Principle:

A square-based pyramidal penetrometer was applied to the nail with the aid of a load P. The mean dimensions of a diagonal of the square imprint obtained with the penetrometer were then determined.

The Vickers hardness (HV) was then determined by the relationship:

$HV = 1854.4 \times P/d^2$ d = mean diagonal in $\mu m$

P = applied load in g

The measurement of the Vickers hardness was performed with the aid of the M 400 g 2 microdurometer from the LECO company.

Procedure:

Fragments of nail were immersed in distilled water for 3 hours and were then left in the ambient moisture for 24 hours.

2 $\mu l$ of a 2.5% weight aqueous solution of citric acid were then applied to the nail. The nails were subsequently placed in an atmosphere of 75% relative humidity for 3 days. The measurement of the Vickers hardness test was then carried out.

A second application of the product and a second measurement of hardness were then performed according to the same conditions described above.

The 2.5% citric acid solution was tested in accordance with this procedure on three samples, in comparison with water (placebo).

Results:

The following results were obtained:

| Treatment | Initial hardness without treatment | Hardness after the first application | Hardness after the second application |
|---|---|---|---|
| Water | 11.8 ± 0.5 | 11.2 ± 0.6 | 10.4 ± 0.9 |
| citric acid | 12.3 ± 0.3 | 10.4 ± 0.6 (−15.4%) | 10.3 ± 0.8 (−16.3%) |

The reported values correspond to the mean obtained for three samples. The figures in brackets indicate the reduction in the hardness of the treated nail when compared with the nail before treatment.

It was found that the hardness of the nails was reduced substantially following treatment with citric acid.

These tests confirm that hydroxy carboxylic acids have the property of reducing the hardness of nails and therefore of softening them.

EXAMPLE 2

A comparison was made of three compositions (A, B, C) comprising citric acid in different proportions (1%, 3%, 8%, respectively) relative to a similar composition (D) devoid of citric acid.

The following compositions were tested:

| Composition | A (novel) | B (novel) | C (not novel) | D (placebo) |
|---|---|---|---|---|
| citric acid | 1 | 3 | 8 | 0 |
| nitrocellulose | 11 | 11 | 11 | 11 |
| resins and plasticizers | 16.6 | 16.6 | 16.6 | 16.6 |
| UV screening agent | 0.2 | 0.2 | 0.2 | 0.2 |
| Solvents | 71.2 | 69.2 | 64.2 | 72.2 |

Each composition was applied to the nails, and the ease of application of the composition, the drying time, the appearance of the film after drying, and the state of the varnish film were determined.

The results obtained were as follows:

| Composition | A (novel) | B (novel) | C (not novel) | D (placebo) |
|---|---|---|---|---|
| application | easy | easy | less easy | easy |
| drying | 15 min. | 15 min. | 15 min. | tacky after 1 h |
| appearance of the film | transparent | transparent | transparent | translucent |
| state of the film | good hold | good hold | good hold | film very weak and flaky |

The gloss, drying time, and hardness of the varnish film were also determined for each composition.

The gloss was measured for a film of 150 $\mu m$ in thickness after drying on a plate thermostatically controlled at 30° C., using a BYK GARDNER Multiangle gloss meter, the beam angle being 60° C. The higher the measured value, the greater the gloss of the film.

The hardness was measured using the Persoz pendulum in accordance with the standard UF-T-30-016.

The drying time was determined by applying 150 $\mu m$ of composition to a bench thermostatically controlled at 30° C.

The results obtained were as follows:

| Composition | A (novel) | B (novel) | C (not novel) | D (placebo) |
|---|---|---|---|---|
| gloss | 90 | 70 | 35 | 90 |
| drying time (min) | 10 to 12 | 10 to 12 | >25 | 4 to 6 |
| hardness | 50 | 45 | 35 | 100 |

The results obtained show that only compositions A and B according to the invention, compared with composition C of the prior art, was applied easily to the nail and made it possible to obtain a varnish film which dried rapidly and and was transparent and glossy. The varnish also exhibited a good hold and was not peelable.

EXAMPLE 3

| A colourless base which had the following composition was prepared | | |
|---|---|---|
| nitrocellulose | | 15 g |
| plasticizer and resin | | 15 g |
| isopropyl alcohol | | 9 g |
| citric acid | | 1 g |
| solvent (ethyl acetate, butyl acetate) | q.s. | 100 g |

After application of the composition to the nail and after drying, a smooth and homogeneous film was obtained.

This composition was applied every 3 days to hard nails for 8 weeks.

Before each application the previous film was removed from the nails with the aid of a conventional remover.

It was found that the nails thus treated were rendered supple.

We claim:

1. A nail treatment composition comprising at least one hydroxy carboxylic acid compound, wherein said at least one hydroxy carboxylic acid compound is a hydroxy carboxylic acid or a salt of said hydroxy carboxylic acid, wherein the concentration of said at least one hydroxy carboxylic acid compound is sufficient to achieve a reduction in hardness of a nail, and further wherein the concentration is sufficient to achieve desirable cosmetic properties, said concentration ranging from 0.5% to 3% by weight, relative to the total weight of the composition.

2. A nail treatment composition according to claim 1, wherein said at least one hydroxy carboxylic acid compound is α-hydroxy carboxylic acid or a salt of said α-hydroxy carboxylic acid.

3. A nail treatment composition according to claim 1, wherein said at least one hydroxy carboxylic acid compound has from 2 to 8 carbon atoms.

4. A nail treatment composition according to claim 3, wherein said at least one hydroxy carboxylic acid compound has from 2 to 5 carbon atoms.

5. A nail treatment composition according to claim 1, wherein said salt of said hydroxy carboxylic acid is a salt with an organic base or with an alkali metal.

6. A nail treatment composition according to claim 1, wherein said hydroxy carboxylic acid is glycolic acid, lactic acid, malic acid, tartaric acid, citric acid or mandelic acid.

7. A nail treatment composition according to claim 6, wherein said hydroxy carboxylic acid is citric acid.

8. A nail treatment composition according to claim 1, wherein said at least one hydroxy carboxylic acid compound is present in a concentration ranging from 0.8% to 2.5%, by weight relative to the total weight of the composition.

9. A nail treatment composition according to claim 1, wherein said composition further comprises at least one vehicle, wherein said at least one vehicle is an organic solvent, water or oil.

10. A nail treatment composition according to claim 1, wherein said composition further comprises at least one film-forming polymer, wherein said at least one film-forming polymer is a nitrocellulose, a cellulose acetobutyrate, a polyvinylbutyral compound, an alkyd resin, a polyester, an acrylic or a polyurethane.

11. A nail treatment composition according to claim 10, wherein said at least one film-forming polymer is present in a concentration ranging from 1 to 40% by weight, relative to the total weight of the composition.

12. A nail treatment composition according to claim 10, wherein said composition further comprises at least one plasticizer.

13. A nail treatment composition according to claim 12, wherein said at least one plasticizer is present in a concentration ranging from 1 to 40% by weight, relative to the total weight of the composition.

14. A nail treatment composition according to claim 1, wherein said composition further comprises at least one adjuvant.

15. A method for reducing the hardness of a nail comprising the step of contacting said nail with an amount of a composition according to claim 1 sufficient to achieve a reduction in hardness of a nail, and further sufficient to achieve desirable cosmetic properties.

16. A method for reducing the hardness of a nail according to claim 15, wherein said amount sufficient to achieve a reduction in hardness of a nail, and further sufficient to achieve desirable cosmetic properties ranges from 0.5% to 3%, relative to the total weight of the composition.

17. A method for reducing the hardness of a nail according to claim 16, wherein said amount sufficient to achieve a reduction in hardness of a nail, and further sufficient to achieve desirable cosmetic properties ranges from 0.8% to 2.5%, relative to the total weight of the composition.

18. A nail treatment composition according to claim 6, wherein said hydroxy carboxylic acid is glycolic acid, lactic acid, citric acid or mandelic acid.

* * * * *